United States Patent [19]

Sarantakis

[11] 4,104,267
[45] Aug. 1, 1978

[54] SOMATOSTATIN ANALOGS

[75] Inventor: Dimitrios Sarantakis, West Chester, Pa.

[73] Assignee: American Home Products Corporation, New York, N.Y.

[21] Appl. No.: 830,930

[22] Filed: Sep. 6, 1977

Related U.S. Application Data

[63] Continuation-in-part of Ser. No. 770,953, Feb. 22, 1977, abandoned.

[51] Int. Cl.² ..................... C07C 103/52; A61K 37/00
[52] U.S. Cl. .............................. 260/112.5 S; 424/177
[58] Field of Search .................. 260/112.5 S; 424/177

[56] References Cited

FOREIGN PATENT DOCUMENTS 7,602,395 9/1976 Netherlands ..................... 260/112.5 S

OTHER PUBLICATIONS

Rivier et al., B.B.R.C. 65, 746 (1975).
Rivier et al., S. Med. Chem. 18, 123 (1975).

Primary Examiner—Delbert R. Phillips
Attorney, Agent, or Firm—Richard K. Jackson

[57] ABSTRACT

Somatostatin analogs which contain L-His[4]-L-His[5] amino acid residues in place of the normally present L-Lys[4]-L-Asn[5] residues are disclosed. Other modifications of somatostatin are also disclosed.

These compounds inhibit the release of pituitary growth hormone, glucagon, and insulin.

10 Claims, No Drawings

SOMATOSTATIN ANALOGS

CROSS-REFERENCE TO COPENDING APPLICATION

This application is a continuation-in-part of copending application Ser. No. 770,953, filed Feb. 22, 1977 now abandoned.

BACKGROUND OF THE INVENTION

The cyclic somatotropin-release inhibiting factor (SRIF), known as somatostatin, has been shown [Brazeau et al., Science, 179, 77 (1973)] to have the following structure:

$$\text{H-Ala-Gly-Cys-Lys-Asn-Phe-Phe-Trp-Lys-Thr-Phe-Thr-Ser-Cys-OH}$$
$$\text{S}\underline{\hspace{5cm}}\text{S}$$

all amino acids being of the "natural" or L configuration.

Several methods for synthesizing somatostatin have been reported in the literature including the solid phase method of Rivier, J. Am. Chem. Soc., 96, 2986 (1974), and the solution methods of Sarantakis et al., Biochemical Biophysical Research Communications, 54, 234 (1973), and Immer et al., Helv. Chim. Acta, 57, 730 (1974); and there is much on-going peptide research whose goal is to enhance somatostatin's pharmacological activity by synthetically modifying its structure.

The present invention provides novel analogs of somatostatin wherein the Ala$^1$-Gly$^2$ residue is either present or may be replaced with H. L-Ala-Gly, L-Ala-D-Ala, Gly-Gly-Gly, or Gly-Gly; the L-Trp$^8$ residue is either present or may be replaced with DTRP$^8$; the L-Lys$^4$-L-Asn$^5$ residues are replaced with L-His$^4$-L-His$^5$ residues; and the L-Cys$^{14}$ residue is either present or may be replaced with D-Cys$^{14}$.

Replacement of the L-Trp residue is somatostatin by D-Trp$^8$ is discussed by J. Rivier et al., Biochem. Biophys. Res. Commun., 65, 746 (1975).

Somatostatin analogs wherein the L-Lys$^4$-L-Asn$^5$ residues are replaced with various other amino acid residues are disclosed in Belgian Pat. No. 839,405.

SUMMARY OF THE INVENTION

The invention sought to be patented resides in the concept of a chemical compound of the formula:

$$\text{X—L—Cys(SA)—L—His—L—His—L—Phe—L—Phe—X}^1\text{—L—Lys—L—Thr—L—Phe—L—Thr—L—Ser—X}^2\text{(SA)—OH}$$

wherein A is hydrogen or the two A groups form a direct bond between the sulfur atoms; X is H, L-Ala-Gly, L-Ala-D-Ala, Gly-Gly-Gly, or Gly-Gly; X$^1$ is L-Trp, or D-Trp; X$^2$ is L-Cys, or D-Cys; and the pharmacologically acceptable salts thereof.

The tangible embodiments of the invention possess the inherent physical properties of being white to light tan colored solids, and substantially insoluble in chloroform, benzene, and the like, but exhibit solubility in water and aqueous acid solutions such as hydrochloric and acetic. The compositions of the invention display no clearly discernable melting points and may be purified by, for example, chromatographic means. Hydrolysis of the compositions of the invention in, for example, 4 N methane-sulfonic acid allows determination of their amino acid content, which is consistent with the structures as hereinbefore set forth.

The tangible embodiments of the invention possess the applied use characteristic of inhibiting the release of the hormones somatotropin, glucagon, and insulin as evidenced by standard pharmacological test procedures.

In addition, the tangible embodiments of the invention may be utilized in admixture with insulin for treating a warmblooded animal suffering from diabetes mellitus.

The invention sought to be patented in a subgeneric aspect resides in the concept of a chemical compound of the formula:

$$\text{H—L—Cys(SA)—L—His—L—His—L—Phe—L—Phe—X}^1\text{—L—Lys—L—Thr—L—Phe—L—Thr—L—Ser—X}^2\text{(SA)—OH}$$

wherein A is hydrogen or the two A groups form a direct bond between the sulfur atoms; X$^1$ is L-Trp, or D-Trp; X$^2$ is L-Cys, or D-Cys; and the pharmacologically acceptable acid addition salts thereof.

The invention sought to be patented in a first specific aspect resides in the concept of the chemical compound which is:

$$\text{H—L—Cys(SH)—L—His—L—His—L—Phe—L—Phe—L—Trp—L—Lys—L—Thr—L—Phe—L—Thr—L—Ser—L—Cys(SH)—OH}$$

The invention sought to be patented in a second specific aspect resides in the concept of the chemical compound which is:

$$\text{H—L—Cys—L—His—L—His—L—Phe—L—Phe—L—Trp—L—Lys—L—Thr—L—Phe—L—Thr—L—Ser—L—Cys—OH}$$
$$\text{S}\underline{\hspace{5cm}}\text{S}$$

The invention sought to be patented in a third specific aspect resides in the concept of the chemical compound which is:

$$\text{H—L—Cys(SH)—L—His—L—His—L—Phe—L—Phe—D—Trp—L—Lys—L—Thr—L—Phe—L—Thr—L—Ser—L—Cys(SH)—OH}$$

The invention sought to be patented in a fourth specific aspect resides in the concept of the chemical compound which is:

$$\text{H—L—Cys—L—His—L—His—L—Phe—L—Phe—D—Trp—L—Lys—L—Thr—L—Phe—L—Thr—L—Ser—L—Cys—OH}$$
$$\text{S}\underline{\hspace{5cm}}\text{S}$$

The invention sought to be patented in a fifth specific asepct resides in the concept of the chemical compound which is:

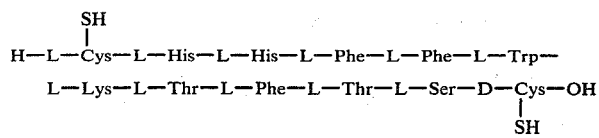

The invention sought to be patented in a sixth specific aspect resides in the concept of the chemical compound which is:

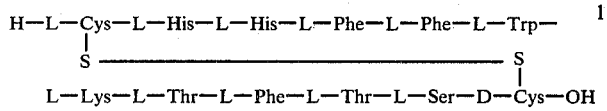

The invention sought to be patented in a seventh specific aspect resides in the concept of the chemical compound which is:

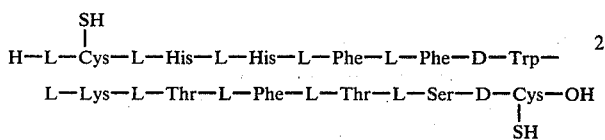

The invention sought to be patented in an eighth specific aspect resides in the concept of the chemical compound which is:

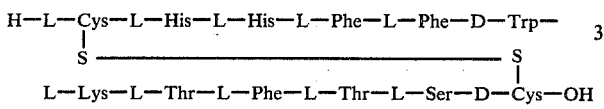

DESCRIPTION OF THE INVENTION

The polypeptide final products and their requisite intermediates are prepared by the well-known solid phase method as described by, for example, Merrifield, J. Am. Chem. Soc., 85, 2149 (1963). As applied to the compounds of this invention, α-amino and sulfhydryl protected cysteine is first attached to a chloromethylated polystyrene resin followed by removal of the α-amino protecting group with trifluoroacetic acid in methylene chloride, trifluoroacetic acid alone or HCl in dioxane. The deprotection is conducted at a temperature between about 0° C. and room temperature. Other standard cleaving reagents and conditions for removal of specific α-amino protecting groups may be used as described in Schroder E. Lubke, "The Peptides," 1, 72–75 (Academic Press, 1965). After removal of the α-amino protecting group, the next desired protected amino acids are coupled individually to the resin supported sequence, seriatim. Alternatively, small peptide fragments may be prepared by, for example, the solution method and introduced into the solid phase reactor in the desired order. Each protected amino acid or amino acid sequence is introduced into the solid phase reactor in about a four fold excess. The coupling is carried out in dimethylformamide, methylene chloride, or a mixture of the two solvents. The success of each coupling reaction at each stage of the synthesis is determined by the ninhydrin reaction as described by E. kaiser et al., Analyt. Biochem., 34, 595 (1970). Where incomplete coupling has occurred, the reaction is repeated before the α-amino protecting group is removed for introduction of the next amino acid or amino acid sequence.

The preferred coupling reagents are 1-hydroxybenzotriazole and diisopropylcarbodiimide; other such reagents will be familiar to those skilled in the art.

After the desired amino acid sequence has been synthesized, the polypeptide is removed from the resin support by treatment with, for example, hydrogen fluoride and anisole to obtain the fully deprotected linear polypeptide. The cyclic disulfide may be produced by air oxidation, or, for example, by oxidation with $K_3Fe(CN)_6$.

Non-toxic addition salts of the linear and cyclic polypeptides are produced by methods well-known in the art from hydrochloric, hydrobromic, sulfuric, phosphoric, polyphosphoric, maleic, acetic, citric, benzoic, succinic, malonic, or ascorbic acid and the like. The acetic acid salt is preferred.

The protecting groups employed throughout the solid phase synthesis are well-known to the art. The α-amino protecting groups employed with each amino acid introduced in sequence of the ultimate polypeptide are of the (1) acyl type protecting groups illustrated by the following: formyl, trifluoroacetyl, phthalyl, p-toluenesulfonyl (tosyl), nitrophenylsulfenyl, etc.; (2) aromatic urethane type protecting groups illustrated by benzyloxycarbonyl and substituted benzyloxycarbonyl such as p-chlorobenzyloxycarbonyl, p-nitrobenzyloxycarbonyl; (3) aliphatic urethane protecting groups illustrated by tert-butyloxycarbonyl, diisopropylmethoxycarbonyl, isopropyloxycarbonyl, allyloxycarbonyl, 2,2,2-trichloroethoxycarbonyl, amyloxycarbonyl; (4) cycloalkyl urethane type protecting groups illustrated by cyclopentyloxycarbonyl, adamantyloxycarbonyl, cyclohexyloxycarbonyl; (5) thiourethane type protecting groups such as phenylthiocarbonyl; (6) alkyl type protecting groups as illustrated by triphenylmethyl (trityl); (7) trialkylsilane groups such as trimethylsilane. The preferred α-amino protecting group is tert-butyloxycarbonyl.

The imidazole nitrogen atom of histidine, denoted $N^{im}$ is protected by a group which may be tosyl, benzyloxycarbonyl, adamantyloxycarbonyl or tert-butyloxycarbonyl, preferably the tosyl group.

Protection for the side chain amino group of lysine may be by tosyl, t-amyloxycarbonyl, t-butyloxycarbonyl, diisopropyloxycarbonyl, benzyloxycarbonyl, halobenzyloxycarbonyl, nitrobenzyloxycarbonyl, and the like, the 2-chlorobenzyloxycarbonyl group being preferred.

Protection for the hydroxyl group of threonine and serine may be with the acetyl, benzoyl, tert-butyl, benzyl. The benzyl group is preferred for this purpose.

The protecting group for the sulfhydryl group of the cysteinyl amino acid residue is a group selected from the class consisting of benzyl; substituted benzyl wherein the substituent is at least one of methyl, methoxy, nitro, or halo (e.g. 3,4-dimethylbenzyl, p-methoxybenzyl, p-chlorobenzyl, p-nitrobenzyl, etc.); trityl, benzyloxycarbonyl, benzhydryl, p-methoxybenzyloxycarbonyl, benzylthiomethyl, ethylcarbamoyl, thioethyl, tetrahydropyranyl, acetamidomethyl, benzoyl, s-sulfonic salt, etc.; the p-methoxybenzyl group being preferred.

The compositions of the instant invention, similar to somatostatin itself, may exist in either the monomeric open chain form (the so called "reduced" form), or the monomeric cyclic form (the so called "oxidized" form). Each of these forms may be produced by a procedure substantially identical to that utilized to obtain the corresponding form of somatostatin itself. These procedures will be familiar to those skilled in the art. The "reduced" form is herein represented by the structure wherein "A" is hydrogen; thus there are free thiol substituents on the two Cys amino acid residues. The "oxidized" form is herein represented by the same structure when the two "A" groups represent a direct bond, i.e. there is a single bond between the sulfur atoms borne on the two Cys amino acid residues, thus a monomeric cycle is formed.

In addition, the compounds of the invention can exist in a so-called "polymeric reduced" form. (See, for example, U.S. Pat. No. 3,926,937), which form can be obtained by the procedure described in the art for the obtention of polymeric reduced somatostatin. Said polymeric form can be described by the formula:

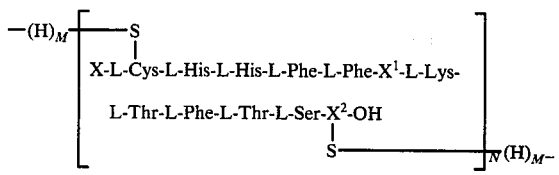

wherein X is H, L-Ala-Gly, L-Ala-D-Ala, Gly-Gly-Gly, or Gly-Gly; $X^1$ is L-Trp, or D-Trp; $X^2$ is L-Cys, or D-Cys, M is O or 1; N is an integer of from 2 to 100 inclusive; and the pharmacologically acceptable salts thereof. In the bracketed structure, where X is other than H, the sulfur-sulfur bonds are randomly formed between $Cys^3$-$Cys^3$, $Cys^3$-$Cys^{14}$, and $Cys^{14}$-$Cys^{14}$ (where X is H, $Cys^1$ instead of $Cys^3$). The structure is cyclic whem M is O, i.e. the compound contains no free SH groups and there is a bond between the sulfur atoms borne on the terminal Cys residues. For the purposes of this invention, the polymeric reduced forms are qualitatively the full equivalents of the compounds particularly claimed.

The pharmacological activity of the peptides of the invention characterizes the compounds as useful in the treatment of acromegaly and diabetes in the same manner as somatostatin itself. Administration of the peptides may be by conventional routes common to somatostatin and related polypeptides, under the guidance of a physician in an amount dictated by the extent of the dysfunction as determined by the physician. The compounds may be administered alone or in conjunction with conventional pharmaceutically acceptable carriers and adjuvants, in unit dosage form.

As hereinabove disclosed, the compositions of the invention are also useful in admixture with insulin for the treatment of a warm-blooded animal suffering from diabetes mellitus. See, for example, U.S. Pat. No. 3,912,807 which teaches the use of an effective amount of a composition comprising somatostatin admixed with insulin for treating a warm-blooded animal suffering from diabetes mellitus.

In therapeutic use as agents for treating acromegaly, juvenile diabetes, and diabetes mellitus, the treatment is initiated with small dosages which are less than the optimum dose of the compound. Thereafter, the dosage is increased by small increments until the optimum effect under the circumstances is reached. In general, the compounds of the invention are administered at a dosage level which will generally afford effective results without causing any harmful or deleterious side effects. The dosages, however, may be varied depending upon the requirements of the patient and the compound being employed. For convenience, the total daily dosage may be divided and administered in portions during the day if desired.

The following examples further illustrate the best mode contemplated by the inventor for the practice of the invention.

EXAMPLE 1 tert-Butyloxycarbonyl-S-p-Methoxybenzyl-L-Cysteinyl-$N^{im}$-Tosyl-L-Histidyl-$N^{im}$-Tosyl-L-Histidyl-L-phenylalanyl-L-phenylalanyl-D-Tryptophyl-$N^\epsilon$-2-Chlorobenzyloxycarbonyl-L-Lysol-O-Benzyl-L-Threonyl-L-Phenylalanyl-O-Benzyl-L-Threonyl-O-Benzyl-L-Seryl-S-p-Methoxybenzyl-L-Cysteinyl Hydroxymethylpolystyrene Chloromethylated polystyrene resin (Lab Systems, Inc.) 1% cross-linked with divinylbenzene was esterified with BOC-Cys(SMBzl)OH according to Gisin, Helv. Chim. Acta, 56, 1976 (1973). The polystyrene resin ester was treated according to Schedule A for the incorporation of BOC-Ser(Bzl)OH, BOC-Thr(Bzl)OH, BOC-Phe-OH, BOC-Thr(Bzl)OH, BOC-Lys(Clz)OH, BOC-D-Trp-OH, BOC-Phe-OH, BOC-PheOH, BOC-His(Tos)OH, BOC-His)TOS)OH, and BOC-Cys(SMBzl)OH to afford the title peptidoresin.

Schedule A

1. Wash with $CH_2Cl_2 \times 3$.
2. Treat with TFA-$CH_2Cl_2$-EDT (1:1:5%, v/v) for 5 minutes.
3. Treat as in 2 for 25 minutes.
4. Wash with $CH_2Cl_2 \times 3$.
5. Wash with DMF.
6. Treat with 12% TEA in DMF twice for 3 minutes.
7. Wash with DMF
8. Wash with $CH_2Cl_2 \times 3$.
9. Treat with 4 equivalents of the corresponding amino acid derivative in $CH_2Cl_2$-DMF and stir for 5 minutes.
10. Add in two portions 5 equivalents of DIC dissolved in $CH_2Cl_2$ and over a period of 30 minutes. Reaction time 6 hours.
11. Wash with DMF $\times 3$.
12. Wash with $CH_2Cl_2 \times 3$.
13. Test ninhydrin reaction according to Kaiser et al., Annal. Biochem., 34, 595 (1970). In case of incomplete reaction repeat lines 9 to 13 above.

EXAMPLE 2

L-Cysteinyl-L-Histidyl-L-Histidyl-L-Phenylalanyl-L-Phenylalanyl-D-Trptophyl-L-Lysyl-L-Threonyl-L-Phenylalanyl-L-Threonyl-L-Seryl-L-Cysteine Cyclic (1-12) Disulfide The peptidoresin of Example 1 (9 g.) was mixed with anisole (18 mg.) and treated with liquid HF (180 ml.) for 45 minutes in an ice bath. The excess HF was removed in vacuo as fast as possible (ca. 1 hour) and the residue was extracted with deaerated 2M-glAcOH then filtered. The filtrate was washed with ether and the aqueous layer was oxidized with $K_3Fe(CN)6$ at a pH 7. The excess oxidant was removed by ion exchange resin Bio Rad Ag-3 then the peptide was absorbed on an ion exchange resin Bio Rex 70 and eluted with a pyridine buffer pH 7 to give after lyophilization 1.5 g. of material. This material was applied onto a column of Sephadex G 15 (2.5 cm. × 160 cm.) and eluted with 15% aq. AcOH. The fractions (5.2 ml. each) in tubes 88–90 were pooled and lyophilized to yield the title compound, 174 mg.

$R_f$(BWA, 4:1:1 ) 0.45
$R_f$(BWAP, 30:24:6:20) 0.64

Amino Acid Analysis: Thr(2)1.87, Ser(1)0.89, Cys(2)1.16, Phe(3)3, Lys(1)1.05, His(2)1.76, Trp ND.

The in vivo pharmacological activity of the dodecapeptide prepared in Example 2 (denoted compound I) was established by the following procedures with the indicated results:

Suppression of Growth Hormone

A subcutaneous (sc) injection of peptide solubilized or suspended in physiological saline, is given to Charles River (CD ®) nonfasted male rats. Matched saline control solution sc injected rats serve as control animals so that every experimental rat is paired with a control rat. The rats are kept in separate cages and 20 minutes before the end of the test time period they are given an intraperitoneal (i.p.) injection of Nembutal ® at a dose of 50 mg/kg. Blood samples are obtained by cardiac puncture and the plasma separated for the radioimmunoassay of growth hormone (GH) concentration (ng/ml.). Time periods after injection of 2 and 4 hours are used to test the duration of the activity of the peptide to suppress circulating peripheral GH levels. Comparisons between control and experimental GH values at each time are evaluated by the Student "$t$" test and statistical significance (p) at the 0.05 level or lower is used as the index of activity.

| Compound (Dose) | 2 Hr. | 4 Hr. |
|---|---|---|
| Control | 118 ± 20 | 115 ± 23 |
| I (1 mg/kg.) | 32 ± 6 | 62 ± 13 |
| | p = <0.01 | p = <0.01 |

Suppression of Growth Hormone, Glucagon and Insulin

Albino male rats are arranged in the three groups (nine rats/group) and injected i.p. with nembutal at 50 mg/kg. Fifteen minutes after the nembutal injection they are injected s.c. according to group with (a) test compound, typically 10–2000 μg/kg.; )b) SRIF 200 μg/kg.; or (c) physiological saline. Ten minutes. later 0.5 ml. of arginine (300 mg/ml. pH 7.2) is injected into the heart. The rats are decapitated five minutes after receiving the arginine, and the blood is collected into Trasylol-EDTA. Appropriate aliquots are then assayed for growth hormone, glucagon and insulin. An active compound is one which significantly changes the plasma level of any of these hormones from that of the saline controls. Comparisons between control and experimental values are statistically evaluated by the analysis of variants method and statistical significance (p) at 0.05 or lower is used as the index of activity.

| Compound (Dose μg/kg.) | GH(ng/ml.) | Insulin (μU/ml.) | Glucagon (pg/ml.) |
|---|---|---|---|
| Control | 163 ± 29 | 278 ± 32 | 69 ± 13 |
| I (100) | 20 ± 8 | 202 ± 49 | 20 ± 8 |
| | p = <0.01 | p = >0.05 | p = <0.01 |

EXAMPLE 3 tert-Butyloxy-Carbonyl-S-p-Methoxybenzyl-L-Cysteinyl-im-Tosyl-LHistidyl-im-Tosyl-L-Histidyl-L-Phenylalanyl-L-Phenylalanyl-D-Tryptophyl-ε-2-Chlorobenzyloxycarbonyl-L-Lysyl-O-Benzyl-L-Threonyl-L-Phenylalanyl-O-Benzyl-L-Threonyl-O-Benzyl-L-Seryl-S-p-Methoxybenzyl-D-Cysteinyl-Hydroxymethyl Polystyrene Ester Chloromethylated polystyrene resin (Lab Systems, Inc.) 1% cross-linked with divinylbenzene was esterified with Boc-D-Cys(SMBzl)OH according to Gisin, Helv. Chim, Acta, 56, 1976 (1973). The polystyrene resin was treated according to Schedule A for the incorporation of Boc-Ser(Bzl)OH, Boc-Thr(Bzl)OH, Boc-Phe-OH, Boc-Thr(Bzl)OH, Boc-Lys(CIZ)OH, Boc-D-Trp-OH, Boc-Phe-OH, Boc-Phe-OH, BOC-His(TOS)OH, Boc-His(Tos)OH and Boc-Cys(SMBzl)OH, to afford the title peptidoresin.

EXAMPLE 4

L-Cysteinyl-L-Histidyl-L-Histidyl-L-Phenylalanyl-L-Phenylalanyl-D-Tryptophyl-L-Lysyl-L-Threonyl-L-Phenylalanyl-L-Threonyl-L-Seryl-D-Cysteine Cyclic (1–12) Disulfide, Diacetate Salt The peptidoresin of the previous example (10 g.) was mixed with anisole (20 ml.) and treated with liquid HF (150 ml.) in an ice-bath for 45 minutes and with exclusion of air. The excess liquid HF was removed under vacuo and the residue was taken in 50% aqueous AcOH. The mixture was filtered and the filtrate was diluted with water to 3.5 liters. The pH was adjusted to 7 with dilute $NH_4OH$ and the disulfhydryl peptide was oxidized with $K_3FE-(CN)_6$, to cyclic disulfide. The pH of the mixture was adjusted to 5 with glacial AcOH and treated with Bio-Rad AG 3. The peptidic material was absorbed onto Bio Rex 70 ($H^+$ form) and eluted with pyridine buffer ($Py-H_2O-AcOH$, 30:66:4, v/v). The fractions containing peptidic material were pooled and lyophilized to yield 1.6 g. of crude material. This crude product was applied onto a column of sephadex LH-20 (2.5 × 90 cm.) and eluted with 10% aqueous AcOH (fractions 5.8 ml. each). The material which emerged in fractions 97–101 was pooled and lyophilized to yield the title dodecapeptide, 171 mg.

TLC, Avicel precoated glass plates, Rf (BWA, 4:1:1, v/v) 0.32 Rf (BWAP, 30:24:6:20, v/v) 0.56.

Amino Acid Analysis: Thr(2)1.85, Ser(1)0.84, Cys(2)1.29, Phe(3)3, Lys(1)1.05, His(2)1.41, Trp(1)0.75.

The in vivo pharmacological activity of the dodecapeptide prepared in Example 4 (denoted Compound II) was established by the procedures detailed at the conclusion of Example 2. The data obtained is as follows:

| | Suppression of Growth Hormone | |
|---|---|---|
| Compound (Dose) | 2 Hr. | 4 Hr. |
| Control | 127 ± 22 | 59 ± 20 |
| II (1 mg/kg.) | 20 ± 3** | 107 ± 34 |

** p <0.001

Suppression of Growth Hormone, Glucagon and Insulin

-continued

| Compound (Dose (μg/kg.) | GH (ng/ml.) | Insulin (μU/ml.) | Glucagon (pg/ml.) |
|---|---|---|---|
| Control | 279 ± 53 | 323 ± 30 | 42 ± 6 |
| II (100) | 64 ± 20* | 165 ± 21* | 5 ± 2* |
| Control | 201 ± 35 | 397 ± 36 | 117 ± 11 |
| II (10) | 110 ± 22+ | 318 ± 54 | 70 ± 7* |

*p <0.01
+p <0.05

From this it is seen that at low doses, Compound II is specific for the suppression of glucagon and growth hormone without affecting insulin secretion.

The subject matter which the Applicant regards as his invention is particularly pointed out and distinctly claimed as follows:

1. A chemical compound of the structure:

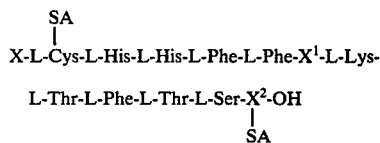

wherein A is hydrogen or the two A groups form a direct bond between the sulfur atoms; X is H, L-Ala-Gly, L-Ala-D-Ala, Gly-Gly-Gly, or Gly-Gly; $X^1$ is L-Trp, or D-Trp; $X^2$ is L-Cys, or D-Cys; and the pharmacologically acceptable acid addition salts thereof.

2. The chemical compounds of claim 1 wherein X is H.

3. The chemical compound of claim 1 which is:

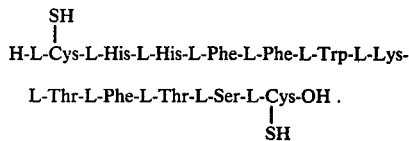

4. The chemical compound of claim 1 which is:

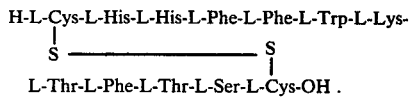

5. The chemical compound of claim 1 which is:

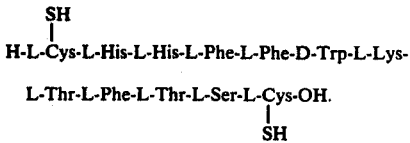

6. The chemical compound of claim 1 which is:

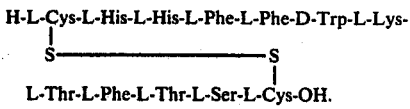

7. The chemical compound of claim 1 which is:

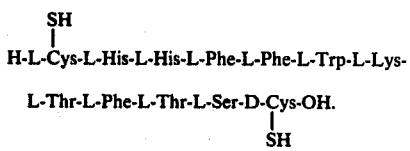

8. The chemical compound of claim 1 which is:

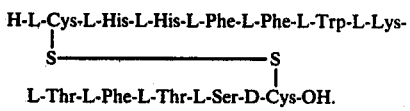

9. The chemical compound of claim 1 which is:

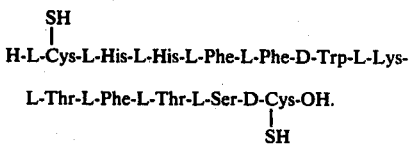

10. The chemical compound of claim 1 which is:

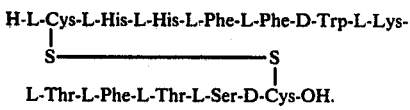

* * * * *